United States Patent [19]
Dewaele

[11] Patent Number: 6,047,257
[45] Date of Patent: Apr. 4, 2000

[54] IDENTIFICATION OF MEDICAL IMAGES THROUGH SPEECH RECOGNITION

[75] Inventor: Piet Dewaele, Berchem, Belgium

[73] Assignee: Agfa-Gevaert, Mortsel, Belgium

[21] Appl. No.: 09/027,365

[22] Filed: Feb. 20, 1998

Related U.S. Application Data

[60] Provisional application No. 60/045,873, May 7, 1997.

[30] Foreign Application Priority Data

Mar. 1, 1997 [EP] European Pat. Off. ............. 97200586

[51] Int. Cl.[7] .............................. G10L 3/00; G03B 42/02
[52] U.S. Cl. .......................... 704/270; 704/272; 250/581
[58] Field of Search .................................... 704/270, 271, 704/272, 275, 235, 260; 250/581

[56] References Cited

U.S. PATENT DOCUMENTS

| | | |
|---|---|---|
| 4,960,994 | 10/1990 | Müller et al. . |
| 5,168,548 | 12/1992 | Kaufman et al. . |
| 5,619,708 | 4/1997 | Ho ......................................... 707/506 |
| 5,646,416 | 7/1997 | Van De Velde ......................... 250/584 |
| 5,654,555 | 8/1997 | Buytaert et al. ........................ 250/581 |
| 5,698,834 | 12/1997 | Worthington et al. ............. 235/472.03 |
| 5,757,021 | 5/1998 | Dewaele .................................. 250/581 |

FOREIGN PATENT DOCUMENTS

| | | |
|---|---|---|
| 0414238 | 2/1991 | European Pat. Off. . |
| 0679909 | 11/1995 | European Pat. Off. . |
| 0699940 | 3/1996 | European Pat. Off. . |
| 0727696 | 8/1996 | European Pat. Off. . |
| 29607856 U | 8/1996 | Germany . |

OTHER PUBLICATIONS

IBM Technical Disclosure Bulletin, vol. 36, No. 3, Mar. 1993, pp. 111–112, XP000354719; "A Method for Speech Recognizer Input to computer Applications in a Windowing System".

IBM Technical Disclosure Bulletin, vol. 36, No. 3, Mar. 1, 1993, pp. 311–312, XP000354789, "Word Translation Profiles for Computer Input from a Speech Recognition System".

*Primary Examiner*—David R. Hudspeth
*Assistant Examiner*—Abul K. Azad
*Attorney, Agent, or Firm*—Baker & Botts, L.L.P.

[57] ABSTRACT

An identification station into which data identifying a medical image are input and by means of which the identification data are associated with the medical image, is provided with a speech recognition subassembly and a microphone to allow data input through speech recognition.

5 Claims, 2 Drawing Sheets

IDENTIFICATION OF MEDICAL IMAGES THROUGH SPEECH RECOGNITION

The application claims the benefit of U.S. Provisional Application No. 60/045,873 filed May 7, 1997.

DESCRIPTION

1. Field of the Invention

The present invention is in the field of medical imaging. The invention relates to identification of medical images, more specifically of radiographic images.

2. Description of Prior Art

When a medical image of a patient is to be produced, a number of identification data are to be associated with said image. Among such data the most relevant are the data identifying the patient to which the image pertains and the data identifying the examination type that is performed or is going to be performed. Other data that are commonly associated with a medical image are the name of the radiologist, the sex of the patient etc.

It is nowadays practice to enter a patient's identification data into a data base, commonly called a hospital information system (HIS). At a subsequent visit of the patient, the data are retrieved from the hospital information system and completed.

In most cases the data entry consists of filling out electronic forms displayed on computer screens.

The current way in which this data entry is performed requires keyboard input or item selection via cursor control keys. This way of operating is inevitably slow, requires correction and may therefore potentially slow down workflow. Even for experienced operators it is impossible to enter more than 25 to 30 words a minute.

The problem becomes more severe when a mobile identification apparatus is used, where keyboard entry is unattractive for additional reasons such as the fact that the mobile identification devices have too small a size to port a normal-size keyboard. So, small keyboards are used having buttons that are too small to allow normal typing speed. Additionally, the key order is in most cases different from the key order on a standard keyboard. Further, the screen size is small so that an awkward user interface navigation is provoked.

Mobile identification apparatuses include hand-held terminals such as PSION Workabout from Psion Ltd., palmtop computers and personal digital assistants. The latter devices sometimes feature pen input capability combined with handwritten recognition instead of keyboard entry. Unfortunately, no 100-percent error free recognition is currently available, requiring difficult-to-operate correction means. Furthermore, its data input speed still remains slow.

Mouse or trackball, another frequently employed means to select items on a graphical user interface, are sometimes available on portable data terminals but are awkward to handle during mobile operation.

A specific medical radiographic imaging technique rapidly gaining importance is digital storage phosphor radiography. According to this technique a radiation image, for example an X-ray image of an object, is stored in a screen comprising a photostimulable phosphor such as one of the phosphors described in European patent application 503 702.

In a read out station the stored radiation image is read by line-wise scanning the screen with stimulating radiation such as laser light of the appropriate wavelength, detecting the light emitted upon stimulation and converting the emitted light into a digital signal representation that can be subjected to different kinds of image processing techniques.

The original or enhanced image can then be transmitted to a hard copy recorder for reproduction of the image on the film size and lay-out of the radiologist's choice and/or it can be applied to a monitor for display.

After read-out the residual image left on the photostimulable phosphor screen is erased so that the screen is again available for exposure.

As in conventional radiography the radiographic image needs to be associated with a patient.

Further, adjustment parameters for the components of the read out device as well as parameters to be used during image processing are to be associated with a radiographic image. Commonly the settings for the read out apparatus and the processing parameters are determined by associating with an X-ray image an identifier of the performed examination type. With this examination type a unique set of read out settings and processing parameters is linked. This set is defined and stored (in the read out apparatus) in advance.

The currently used patient and examination type identification system operates as follows. An unexposed photostimulable phosphor screen is conveyed in a cassette that is provided with an EEPROM having a number of electrical contacts in a fixed position on the cassette for power supply and read-write transfer of identification data. The radiologist or operator performs a radiographic exposure of a phosphor screen in a cassette and transports the exposed cassette to an identification station. The identification data of the patient are entered into an identification program running on the identification station. This can be performed manually by entering the data into a personal computer of the identification system via keyboard entry.

Alternatively, in case the identification station is connected to a hospital information system (HIS) or a radiology information system (RIS), the identification data can be retrieved from that information system.

An examination type identifier is entered manually into the identification station by selecting a specific examination type (and subtype) out of a hierarchically popped up menu.

Then, the patient identification data and the examination type identifier are written into the EEPROM on the exposed cassette by means of dedicated hardware linked to the identification station's personal computer. Further details on this procedure as well as on the outlook of the cassette are described in U.S. Pat. No. 4,960,994.

The exposed and identified cassette is then fed into a read out station that is provided with means for reading out the data stored in the EEPROM and for storing these data in a central memory and with means for reading the radiographic image stored in the photostimulable phosphor screen.

The examination type read out of the EEPROM controls selection of corresponding parameters for set up of the read out electronics as well as for the image processing to be performed on the read out image. These parameters were stored in advance in a look up table in the memory of the read out apparatus following a customization procedure as has been described in European patent application 0 679 909. Next, variable contents of the EEPROM are erased whereas fixed contents are kept or updated.

The image in the screen is read out and subjected to processing taking into account the read-out settings and the processing parameters corresponding with the identified examination type.

Alternatives to the above method have been developed and are described in European patent application 0 727 696. In this patent application several embodiments of patient identification means such as a bar code label, a radio-frequency tag, a touch memory or an EEPROM device have been described. A read/write terminal which is preferably a mobile hand-held terminal is used to read the information in the patient identification means and to transfer this information to a radio-frequency tag provided on a cassette conveying a photostimulable phosphor screen.

The information stored in the different embodiments of the patient identification means is either retrieved from a data base or manually, i.e. via keyboard entry, entered into a computer and transferred from the computer, to a bar code printer or to a RF tag, or a touch memory.

Although these alternatives provide more freedom of operation to the operator who needs to perform the identification of a medical image, all embodiments require keyboard entry at some point during the identification procedure and hence suffer from the already mentioned drawbacks such as low speed, correction requirement, difficult handling etc.

OBJECTS OF THE INVENTION

It is thus an object of the invention to provide an identification station for identifying a medical image and an identification method that is fast and reliable and allows for handsfree operation.

It is a further object of an embodiment of the invention to provide such an identification station and such an identification method that are adapted for use in the field of storage phosphor imaging wherein an image is stored on a photostimulable phosphor screen conveyed in a cassette comprising a cassette identifying means such as an electronic memory.

Still further objects will become apparent from the description hereafter.

STATEMENT OF THE INVENTION

To achieve the above objectives the present invention provides an identification station (1) comprising means (4,5) for entering data identifying a medical image and means (6,18) for associating data with the medical image, characterised in that said means (4,5) for entering data are means for entering data through voice recognition.

Another aspect of this invention relates to a method of identifying a medical image comprising the steps of
  entering identification data of said medical image into an identification station,
  associating said identification data with said medical image, characterised in that said identification data are entered by speech.

An identification station commonly comprises a personal computer or a workstation running an identification program. It can be a stand alone station or a station that is connected to a network and that provides access to a hospital information system or a radiology information system. For the ease of manipulation in a hospital environment the identification station is preferably a portable read/write station.

The identification station according to the present invention is equipped to provide data input through voice recognition.

For this purpose the identification station comprises a speech recognition subassembly and a microphone connected to this subassembly.

A speech recognition subassembly commonly comprises:
  an input for a microphone (e.g. for a condenser or dynamic microphone),
  an analog-to-digital converter for converting data supplied via the microphone input,
  a CPU (an 8 bit microcontroller such as an Intel 8051 or an Intel 8088 can perform the task. Evidently, more performant microprocessors can also be used),
  processing means for processing data converted by the analog-to-digital converter, such as a dedicated DSP processor (e.g. selected from the Texas TMS 320 series processor or AD 21 series or Motorola 56xxx or 88xxx series etc.),
  memory means for data and program storage, for example a ROM memory for program storage and a RAM memory for data storage,
  a power supply,
  and interfacing means such as a RS 232 connection.

Preferably a signal conditioning means (this is an electronic circuit that provides signal amplification etc.) is provided for conditioning the signal that is supplied via the microphone input.

In one embodiment the identification station is also provided with a voice synthesis subassembly and a speaker for providing auditive responses to the operator. Such an assembly additionally comprises a digital to analog convertor, an amplifier, a speaker output and a RAM memory for storing voice samples.

Speech recognition technology has reached the point where affordable commercial speech products are available for desktop systems (see "PDAs and Speech Recognition" in Andrew Seybold's Outlook on Communications and Computing, Vol. 14, No. 10, pp. 9–12).

Data entry speed is much higher than keyboard typing and handwritten recognition. It further allows hand-free and eyes-free operation of the identification equipment enabling the operator to freely communicate without having to have physical contact with identification system for controlling the flow of it or the input of it. Combined with speech synthesis or recall of previously recorded speech samples, speech technology thus enables two-way system interaction solely by means of voice.

Algorithmic advances and DSP (digital signal processing) implementation now provide means for implementing the required voice processing on reasonable cost and reasonable power platforms while maintaining the required accuracy for the application.

Companies offering desktop continuous speech recognition hardware and software, include Dragon Systems in the U.S.A. and Lernout & Hauspie in Belgium. An example of a speech recognition subassembly is the STAR21 stand-alone board from Lernout & Hauspie Speech Products. It is a low cost and complexity product featuring an input for condenser microphone, an Analog Devices AD21msp58 DSP 12 Mhz signal processor, SRAM and Flash memory for program and speech model storage and RS232 connection to a host. Products designed for small hand-held devices are offered by companies such as Advanced Recognition Technologies (ART). The SmartSpeak product of ART is a low-cost voice recognition software package, which is integrated on a board featuring a microphone input, 8 bit A/D converter, a 8051 microcontroller, RAM and ROM memory and a serial RS232 interface.

A strong prejudice has existed against the application of data input via speech for identification purposes. Speech recognition is difficult primarily because of variability, which comes in different forms : (1) variability of sounds (different words, phrases or subword units), (2) transducer/channel variability. Further there is a risk of interference with background noise from extraneous speech or transient acoustic events.

In the field of medical images these prejudices have been overcome because:

(1) the number of words in a medical identification task is restricted to a vocabulary of at most 100 single and isolated words so that the variability of sounds is limited.

(2) transducer/channel variability including differences in signal characterisation is limited since the input is always via microphone, the characteristics of which are known at design stage. Thus, the voice recognition system need not be able to cope with a variety of sources.

(3) the risk of interference with background noise from extraneous speech or transient acoustic events is limited on a radiology department since the voice input is under software control of the application and is restricted to well defined time slots in the course of operation.

Significant advances in several technologies and application areas pertinent to voice processing have made feasible automatic voice recognition, such as (1) smart microphones adapting to any acoustic environment and giving optimum signal-to-noise ratio in noisy backgrounds (2) acoustic echo cancellation to provide echo-free communications (3) advances in algorithms and DSP implementation of these algorithms providing high performance on reasonable cost platform. Although the sources of variability cannot be eliminated in general, speech recognition technology has reached a point to model and handle them properly. These models are based on (1) standard pattern recognition or (2) on hidden Markov models. The first class computes a best match similarity score between a spectral pattern of features against a database of stored vocabulary patterns. These spectral patterns model differences across different speakers and variance statistics derived over the time duration of the word. The second class of models calculates the highest likelihood score for a probabilistic model for each word of a vocabulary of words.

Voice processing has proven to be very well suited for the purpose of identification in a hospital environment or specifically in a radiology department for the following reasons.

First, the speaking format, that is the mode of speaking to the machine has limited complexity : it will basically fall into one of the following categories:

(a) isolated word recognition (each spoken command or data entity represents one single word) or (b) connected word mode (the operator uses fluent speech but with highly constrained vocabulary) or (c) continuous speech mode (the operator dictates phrases or performs a dialogue).

The first mode is suited for control and command entry and for input of single word data, the second mode is suited for entry of letters of the alphabet or digits. The third category of speaking format is continuous speech and is applicable for voice entry of comment-like annotations or clinical protocols to a patient's identification records.

A second reason why voice processing is well suited for identification of medical images is that the degree of speaker dependence is low, since the number of operators is typically low and almost fixed over time.

A third reason is that the vocabulary size and complexity is low to moderate. It will typically consist of a set of command and control words to navigate the user interface of the identification application by appropriate words for operations such as screen selection, cursor movement and key stroke shortcuts. Further, it will consist of sets of words for mandatory inputs such as examination type, sub-examination type, image destination type. Finally, many identification data are letters drawn from the alphabet, or digits such as patient's birthday (digits), patient's sex (letter), patient's index (digits), number of hardcopies requested (digit), image layout parameters (letters or digits).

Fourth, the application task constrains the number of possible words to be recognized. The combinations of examination and sub-examination strings can easily exceed 200. However, entry of the examination type constrains the number of possibilities of the sub-examination types to be recognized to the set of sub-examinations belonging to the examination class just recognized, thereby minimizing false recognition.

In general, some form of task constraints in the form of formal syntax (defining which words can follow other words in different contexts of the identification flow) and formal semantics (defining which words make sense in the current status of the identification operation) make the recognition task more manageable.

The limited size of the vocabulary to be recognized for the radiology identification task enables one to customize the vocabulary as to language and operator. This feature is implemented in a straightforward way by letting the system switch to the appropriate set of stored reference voice patterns whenever the operator identifies himself to the identification system, either upon entry of the operator's name or by automatic speaker recognition of an utterance of the operator's name.

The identification station according to the present invention has been designed in particular for use in connection with a system wherein a medical image is stored in a photostimulable phosphor screen.

However, it can be applied in connection with imaging systems comprising other means for storing medical images such as radiographic film.

Photostimulable phosphor screens are conventionally conveyed in a cassette. In one embodiment such a cassette is provided with a cassette identifying means, for example an electronic memory device. Data identifying the medical image are then input to an identification station according to the present invention and are then transferred from the identification station to the memory on the cassette.

Although the cassette identifying means may take different forms (e.g. bar code label), an electronic memory is very useful because of its storage capacity, its ability to be re-used, etc. A cassette for conveying a storage phosphor, comprising a memory device has been described in European Patent application 0 307 760.

Various forms of electronic memory devices exist such as galvanically connectable EEPROM, touch memory etc.

Devices that permit transfer of data and/or energy by radio-frequency transmission are preferred because these devices allow identification without the need for physical connection between the identification device and the cassette. This kind of devices is furthermore very well adapted for use with a mobile identification apparatus.

A device that is very well suited for such an application is a radio-frequency tag (alternatively termed radio-frequency transponder). Identification procedures based on the use of radio-frequency tags have been described in European patent application 0 727 696.

In case a radio-frequency tag is used, the identification station needs to be equipped with means for transferring identification data to said memory by radio-frequency transmission. Additionally the identification station may be equipped with means for transferring supply voltage to said memory by radio-frequency transmission.

BRIEF DESCRIPTION OF THE DRAWINGS

Particular aspects of the present invention as well as preferred embodiments thereof will be explained by means of the corresponding drawings wherein.

DETAILED DESCRIPTION

Figure 1:
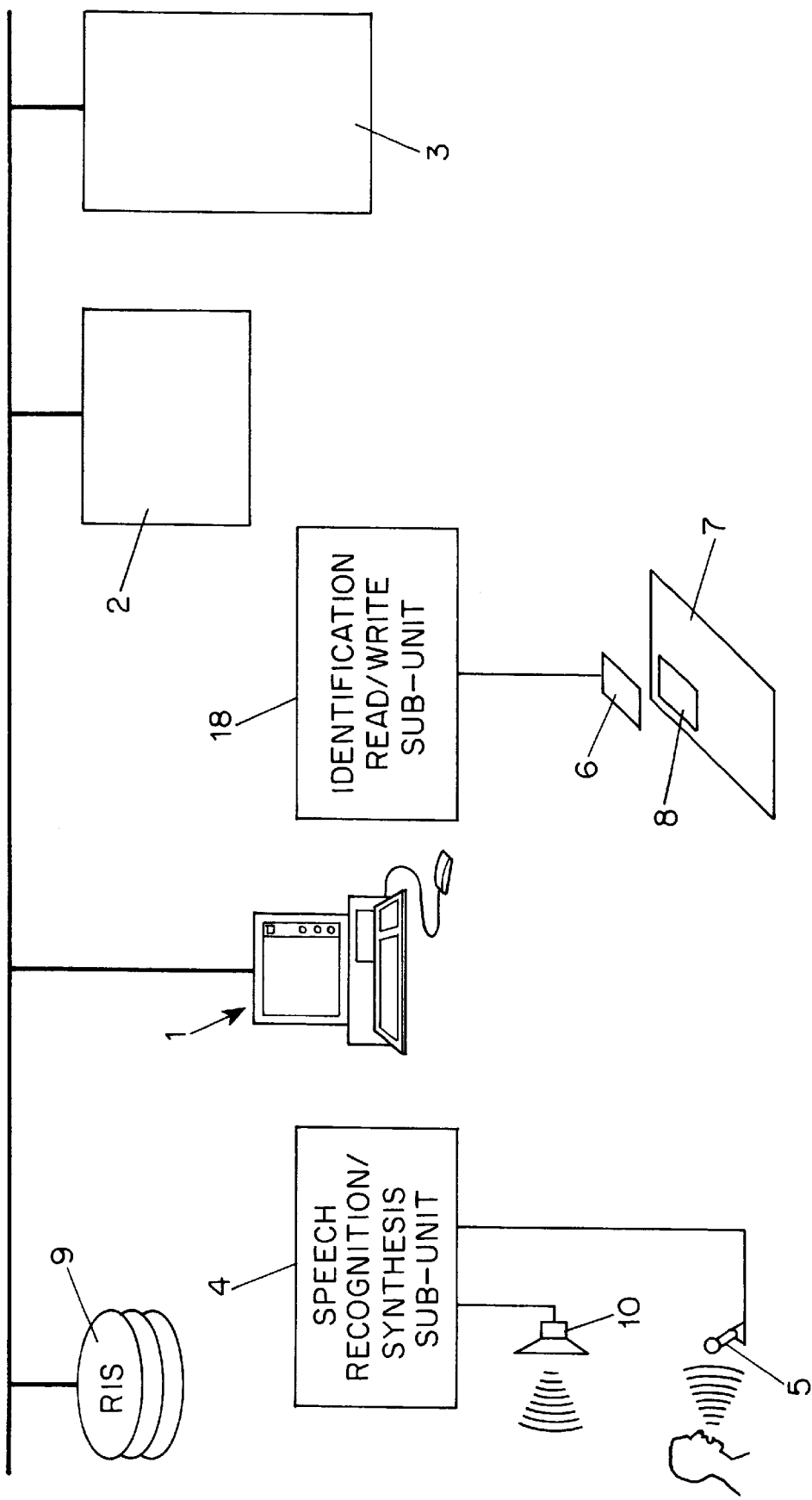
FIG. 1 is a general view of a system in which the method of the present invention can be applied.

A simplified diagram of a system in which the present invention can be implemented, is shown in FIG. 1.

The described system is a digital radiography system wherein a radiographic image is recorded on a photostimulable phosphor screen. The photostimulable phosphor screen is conveyed in a cassette 7. The cassette is provided with a radio-frequency tag 8 in which identification data, i.a. data concerning a patient that is subjected to a radiographic examination and concerning the type of examination that is performed etc., are stored.

The system comprises an identification station 1, a read out station 2 in which the image stored in the photostimulable phosphor screen is read out and digitized and wherein the digital signal representation of the radiographic image is subjected to image processing. A laser recorder 3 is provided for reproducing the read out image.

The system shown in FIG. 1 can be expanded to include other stations such as a workstation for performing off-line processing on the digital representation of the radiographic image and/or for performing soft copy diagnosis. However, since these additional components are not relevant in the context of the present invention, they will not be described in detail.

The identification station 1 consists of a personal computer (or alternatively a workstation) which is in the described embodiment connected to a network so as to provide access to a hospital information system (HIS) or a radiology information system 9 (RIS).

The identification station is further equipped with a speech recognition/synthesis subassembly 4, with a dynamic microphone input 5 to provide data input via speech and a speaker 10 to provide auditive responses. An example of a suitable speech recognition subassembly is a standalone board Star 21 of Lernout and Hauspie (Belgium) with microphone speech input and, an (AD21) DSP, speech models stored in (AMD Flash) memory, RS232 connection to host, amplifier for synthesized TTS (Text to Speech), speech output, power supply.

The personal computer (or workstation) is provided with a read/write sub-unit 18 and an antenna 6 and corresponding steering electronics (not shown) for transferring data to an RF tag. Additionally, a link to a bar code printer, or to a touch probe may be provided. The selection of probes or connections that is provided depends on the mode of operation chosen by a specific hospital.

Figure 2:
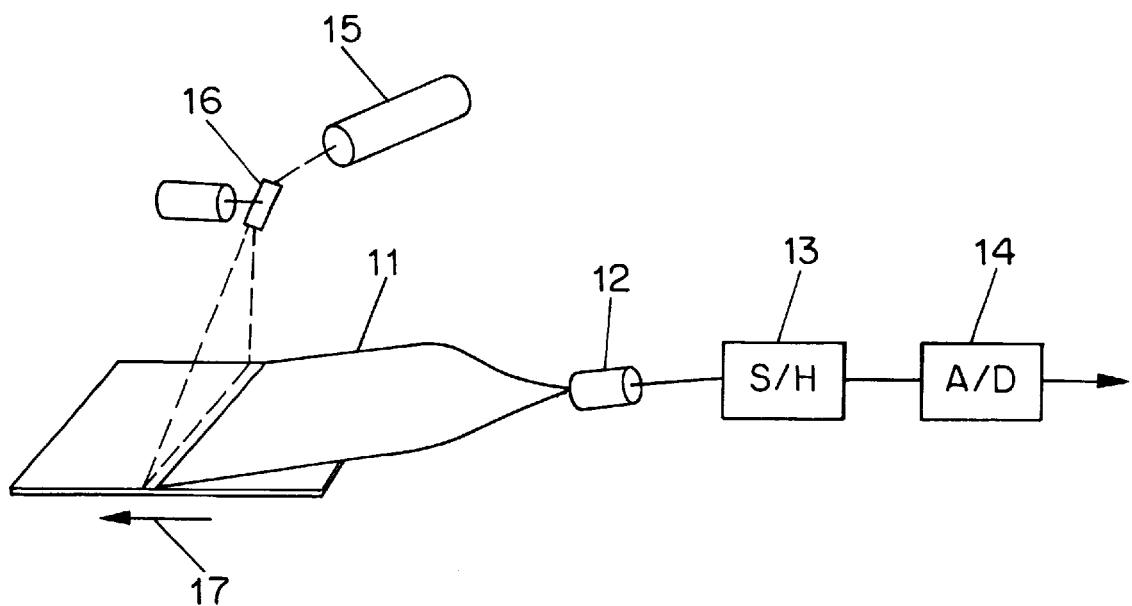
FIG. 2 is a detailed view of a system for reading an image stored in a photostimulable phosphor screen.

The read out station is illustrated in FIG. 2 and comprises a laser 15 emitting light of a wavelength adapted to the stimulation spectrum of the phosphor used, galvanometric light deflection means 16 for deflecting light emitted by the laser onto the photostimulable phosphor screen, a light guide 11 directing light emitted by a stimulable phosphor screen into the light input face of a photomultiplier 12, a sample and hold circuit 13, and an analog to digital convertor 14. The read out device also comprises a processing module (not shown) for performing online processing on the digital signal representation of the radiation image.

The operation of the read out station is as follows. Stimulating rays emitted by laser 15 are directed onto the photostimulable phosphor screen to scan this screen. The stimulating rays are deflected into the main scanning direction by means of galvanometric deflection means 16. Subscanning is performed by transporting the phosphor screen in the subscanning direction indicated by arrow 17. Upon stimulation, the photostimulable phosphor emits light within a second wavelength range which is different from the wavelength range of the stimulation light. The emitted light is directed by means of a light collector 11 onto a photomultiplier 12 for conversion into an electrical image representation. Next, the signal is sampled by a sample and hold circuit 13, and converted into a digital raw image signal by means of an analog to digital convertor 14. The digital signal representation of the radiation image is then fed into processing module (not shown) where it is subjected to image enhancing signal processing techniques.

Workflow Description

The following is a description of the workflow from the identification of a radiation image pertaining to a radiographic examination of a patient to the read out of the digital image representation.

FIRST EMBODIMENT

Stationary Operation

Patient intake. At patient intake some standardized data entry operations are commonly performed to supply subsequently involved hospital entities with requested patient data. Such data entry proceeds by filling out electronic forms displayed on the screen of an identification station. The kind of task is highly repetitive and is generally performed by a small staff of people who train the system to recognize individual word patterns. The task is also characterised in that sequences of keystrokes can be replaced with a single voice command or a voice macro and it is thus a task that is well suited to be handled by voice processing.

Another task commonly performed at the patient reception desk is that of accessing a database such as a RIS or HIS. The recognition task then consists of querying a database to determine specific information concerning the patient contained within the database.

The following actions are considered at patient intake, the third one being specifically aimed at enabling the subsequent use of speech recognition based identification operation in the radiology department:

(a) all patient related data are entered manually in a RIS (Radiological Information System) or HIS (Hospital Information System) by an employee of the administrative department or retrieved by database query and brought up to date;

(b) the list of currently residing patients is updated;

(c) a voice sample of the name of the patient is uttered by the employee and stored along with the index/patient list;

(d) patient or examination specific annotations are entered by voice and stored in the patient's records so as to be recalled by voice synthesis. To the purpose of voice recognition in the ART system the voice sample is digitized in the acquisition phrase by an A/D convertor, as small as 6 bits, and compressed into a package as small as 200 bytes on the average per second of analyzed signal, and stored in memory. Therefore, the RAM storage requirement does not exceed 100 KByte for 500 isolated words. The 200 Byte package is a compressed signature in vector form capturing the features that make a particular sound-bite unique. In the recognition phrase, these vectors are compared by the recognition engine with an input voice sample that is similarly digitized and compressed.

(e) the patient is optionally provided with a personal identification data carrier such as a barcode, encoding the patient index, or an EEPROM based data carrier such as a Touch Memory or an RF-tag.

Patient exposure. The cassette conveying a photostimulable phosphor screen is exposed at an examination site by a radiology operator or a physician. The cassette is provided with an EEPROM based data carrier. In this embodiment the data carrier is a RF tag (radio-frequency tag). Information can be written onto and read from a RF tag without requiring mechanical contact.

Cassette identification. The exposed cassette is then transferred to identification station 1. The identification station consists of a networked personal computer, a read/write identification subassembly (6,7) to write and read data to and from the identification carrier of an introduced cassette and a speech recognition subassembly (4,5) with microphone input (5).

The design of the identification station shown in FIG. 1 is only one example. Alternative designs are possible. The apparatus may for example be provided with a slit wherein a cassette can be slided so that the radio-frequency tag is optimally positioned for wireless data (and energy) transfer. The speech recognition subassembly can either be integrated on a stand-alone board separately powered and connected to the identification station by serial link or it can be integrated on a plug in board in the identification station.

The following is a description of operations performed, along with details pertinent to the voice recognition functionality:

A radiologist specific identification-screen is popped up either by sensing an operator's personal identification carrier to the read/write identification subsystem or by voice recognition of an utterance of the operator's name by the speech recognition subassembly. The database of voice patterns pertaining to the operator is made active.

The patient's name is uttered by the operator to identify the patient to the system. On correct recognition, the name is displayed in the patient name field. On false recognition, an alternative voice input is offered consisting of spelling the patient's name. During utterance of the letters of the name, the list of patients currently residing in the hospital as established during patient intake, is popped up onto the screen. The portion of the list displayed during spelling is continuously narrowed as more successive letters are recognized by the system. In addition to the patient name, the list also shows the running number of the patient in the list and the patient's birthday. At all times during spelling the name, a shortening may be obtained by uttering the digits of the running number of the patient as soon as the data searched for become displayed. Both spelling of 26 letters of the alphabet and the 10 digits is far less prone to recognition error than direct recognition of the patient's name, for reasons that the vocabulary of letters and digits has fixed size and can be specifically trained to the operator. In contrast, direct recognition of the patient's name is more difficult since the number of words is substantially large (as large as 500 e.g.) and since the voice sample of the name used as a reference template, has been recorded by a receptionist at patient intake. This person in general is different from the radiology operator, and patient name recognition thus has presented itself as a speaker independent recognition task. An acceptance qualifier completes the patient entry; a correction qualifiers offers the operator the opportunity to re-enter a name; a rub-out qualifier enables to erase letters in much the same way as the backspace key on a keyboard operates. As a fallback way of entry, the patient name may still be selected by cursor movement from the patient list or entered manually by keyboard on network failure or absence of a RIS database. The patient name is filled in in its appropriate field, and other patient related data are retrieved from the RIS database to complete fields such as sex (M/F) and birthday. Should these latter items be unavailable, voice entry of them is task of recognition of a sequence of letters and digits.

The system prompts the operator to input the examination type. The examination type is one out of a radiologist specific list of examination (such as thorax, pelvis, skull, . . . ) and recognition thus belongs to the isolated word mode. The size of the examination list typically does not exceed 20. On correct recognition, the examination type is automatically entered into the appropriate field. On false recognition, a list of all examination types and a ranking number is popped up to assist the operator in selecting the examination type. Selection now is done by uttering the digits (one or two digits) of the ranking number. Alternatively, the user may use cursor movements to scroll through the list and the 'enter' button to select.

The system then prompts the operator to input the sub-examination type. The sub-examination type is one out of a radiologist specific list of sub-examinations (e.g. 'lateral', 'frontal', . . . ), pertaining to the examination type just selected. The size of the sub-examination list typically does not exceed 25 per examination, still amounting to a total number of sub-examinations as large as 500. However, knowledge of the examination type restricts the number of valid choices for the sub-examination in that sub-examination of other examination classes are not taken into consideration. This makes the recognition of the sub-examination more manageable. Analogously, on correct recognition, the sub-examination type is automatically entered into its field. On false recognition, a list of all examination types and a ranking number is popped up to assist the operator in selecting the sub-examination type by utterance of the corresponding digit sequence.

Examination and sub-examination determine layout parameters as to how the image will be processed, printed and displayed (these include patient position, cassette position and exposure class). These parameters are retrieved from radiologist specific internal data buffers and are automatically filled out in their appropriate fields. Should these fields be modified, the operator issues voice commands as to the placement of the cursor in one of these fields and modifies the default entry.

The system prompts the operator to input the destination type. The destination type is one out of a radiologist specific list of preferred hardcopy and softcopy devices to send the digitized image to. The list typically contains smaller than 10 items. Selection proceeds in a way similar to that of the examination and sub-examination entry. Next, the number of copies on a hardcopy unit is entered by voice.

Optionally, the operator may enter comments in the 'user info' field as a recorded voice stream upon issuing the request "info". Voice data is stored along with other identification data in a database.

On completion of all fields on the identification screen, the system prompts the operator to write the data to the cassette identification carrier by means of the Read/Write subassembly on recognition of the action word "write" or other meaningful answers such as "OK" or "Yes".

A typical voice based identification session is the following sequence

| Identification System | Operator |
|---|---|
| "Please enter operator identification" | "Operator Johnston" |
| "Enter patient" | "Smith" |
| "Unrecognized. Please spell" | "S", "M" |
| (patient list pops up, patient Smith has number 54) | "five", "four" |
| "Enter examination" | "thorax" |
| "Enter sub-examination" | "lateral" |
| "Enter destination" | "list" |
| (list is popped up, LR_3 device has number 3) | "three" |
| "Number of copies" | "two" |
| "Accept and write data?" | "OK" |

Identification data that were input in the identification station and an energy signal for powering the radiofrequency tag on the cassette are transferred through radio-frequency transmission onto the radio-frequency tag provided on the cassette. The identification procedure is now terminated.

Digitization. After identification, the cassette is withdrawn from identification station 1 and entered into read out apparatus 2. The identification data are read out from the radio-frequency tag on the cassette and used for processing the image according to specific image processing parameters pertaining to the examination type.

Should demographic data be unavailable on the cassette id-data carrier, all unknown fields are retrieved from the RIS/HIS database by patient record lookup.

Hardcopy/Softcopy. Patient demographic data, examination processing settings and radiologist name are sent along with the image to the hardcopy unit or transmitted to a softcopy diagnostic unit.

SECOND EMBODIMENT

Mobile Operation

Mobile identification offers the advantage over stationary identification in that the identification can be performed at the examination site. This is particularly advantageous for intensive care units (ICUs) and bedside examinations (e.g. thorax at bed) because it considerably reduces the risk of misidentification.

However, the operator carries both a portable identification terminal and one or more cassettes, and thus faces a manipulation problem, in addition to the problems outline before. Voice based data entry enables him a hands and eyes free mobile identification operation, the details of which are disclosed below.

For the purpose of mobile identification, a handheld computer such as Psion Workabout from Psion Ltd., U.K. is equipped with peripherals as described in "Psion Workabout, Products & Markets document", such as a barcode scanner, a custom designed Touch Memory module to write/read Touch Memory buttons from Dallas Semiconductor, USA, and/or a custom designed RF-tag write/read subunit to write/read RF-tags from MIKRON GmbH, Austria. The terminal is equipped with microphone, A/D converter, microcontroller and voice recognition software such as SmartSpeak available from Advanced Recognition Technologies Inc., USA. The mobile identification modality further comprises a network of docking stations, connected to a host in a serial multidrop network via RS485 or in another common network standard such as Ethernet. The host runs the communication software to communicate with the handhelds. A mobile identification session proceeds in much the same way as a stationary identification operation:

at regular time intervals an updated patient list annotated with patient index and a 200 byte voice sample of the patient name is communicated across the cradle network to all mobile terminals. Alternatively, at all times, the most recent list can be retrieved on request of the operator by a key sequence.

The radiology operator picks up a terminal, and identifies himself to the system, by reading the operator's identification means.

Patient identification is done either by scanning the patient's barcode holding the patient index or by voice input of the patient's name. Analogous to the stationary identification, a similarity score between a compressed version of the operator's utterance of the patient name and all 200 Byte voice compressed samples, attached to the patient name is computed, and the most similar match determines the patient name presented to the operator. Should verification reveal incorrect identification, the patient name is spelled and a list narrows until no more than one patient name corresponds to the sequence of uttered letters. Again, such a task is much less error prone, since it represents a fixed and limited vocabulary recognition task.

Examination, sub-examination and destination are recognized and entered to the system by a procedure analogous to the stationary identification.

The cassette is identified by writing all identification data to the cassette's identification carrier by means of a read/write subunit of the portable terminal, e.g. a RF-tag module.

Further characteristics of the implementation include the following:

operator training and customization: This is the ability to input and store a voice sample of all command words recognized in the application for each operator to tune the system to better accuracy and robustness. At least the following words need be uttered once by an operator previously unknown to the system : 26 letters of the alphabet 'a' . . . 'z', 10 digits '0' . . . '9'; mnemonic qualifiers for control words such as 'enter', 'return', 'accept', 'reject', 'delete', 'exit', 'escape', 'up', 'down', 'left', 'right', 'insert', 'home', 'end', 'shift', 'tab' and mnemonic qualifiers for action words such as 'read', 'write', 'list', 'info'. Control words are used to move the cursor through the screens or through menus of the identification user interface, through successive fields on a screen or between individual characters within a field. Action words are used to let the application perform an action, such as writing the identification data to the identification carrier by means of the Read/Write subassembly.

Storage of voice samples to synthesize voice prompts. These voice prompts consist of standard words "enter", "patient", "examination", "sub-examination", . . . and are used to reconstruct any prompt as a concatenation of any of these words.

Barge-in capability, that is the ability of the operator to speak over the voice prompt, thereby cancelling the prompt. This feature is invaluable for experienced operators who do not need to listen to the prompt to know what to say to the system. Prompting may be switched off completely on operator request.

Word spotting capability, that is the ability to recognize either a command word or a command sequence within fluent speech.

Real-time response, that is short response time (typically less than 1 sec per item) for display of recognized letters, words or command words such that the operator feels in control of the actions of the system.

To secure safe continuation, the identification application asks the operator to aid in error detection and correction whenever the recognizer is ambiguous or not confident of its outcome.

To limit access to the system to authorized persons only and to simultaneously identify the operator for retrieval of the operator's customized identification settings, speaker verification is used. Speaker verification technology determines whether a given speech sample, e.g. the operators name, was spoken by the speaker's claimed identity. An operator wishing to be verified makes an identity claim. This accesses a stored voice pattern for that identity. The system compares the time aligned speech samples of the operator with the stored pattern and computes a similarity or distance score. The degree of match can be used to control operator specific identification data.

The digitization and hard/soft copy recording is identical to the procedure described higher.

I claim:

1. An identification station comprising means for entering data identifying a medical image, means for associating data with the medical image, characterized in that said means for entering data are means for entering data through voice recognition, wherein said medical image is stored in a photostimulable phosphor screen conveyed in a cassette, having an electronic memory, and means for transferring identification data to said electronic memory by radio-frequency transmission.

2. An identification station according to claim 1 wherein said means for entering data through voice recognition comprise a speech recognition subassembly and a microphone connected to said speech recognition subassembly.

3. An identification station according to claim 2 provided with a speech synthesis subassembly and a speaker connected to said speech synthesis subassembly.

4. An identification station according to claim 1 that is portable.

5. A method of identifying a medical image comprising the steps of entering identification data into an identification station, associating said identification data with said medical image, characterized in that said identification data are entered into said identification station by speech, wherein said medical image is stored in a photostimulable phosphor screen conveyed in a cassette, having an electronic memory, and means for transferring identification data to said electronic memory by radio-frequency transmission.

* * * * *